(12) United States Patent
Ryan

(10) Patent No.: US 8,369,935 B2
(45) Date of Patent: Feb. 5, 2013

(54) ECHOGENIC NEEDLE MECHANISM

(75) Inventor: Shawn Ryan, Upton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 239 days.

(21) Appl. No.: 12/883,379

(22) Filed: Sep. 16, 2010

(65) Prior Publication Data
US 2011/0071386 A1 Mar. 24, 2011

Related U.S. Application Data

(60) Provisional application No. 61/245,454, filed on Sep. 24, 2009.

(51) Int. Cl.
*A61B 8/00* (2006.01)
(52) U.S. Cl. .......... 600/424; 600/435; 600/437
(58) Field of Classification Search .......... 600/424, 600/437, 435; 604/272
See application file for complete search history.

(56) References Cited

U.S. PATENT DOCUMENTS

| 4,977,897 | A | 12/1990 | Hurwitz |
| 5,490,521 | A | 2/1996 | Davis et al. |
| 5,820,554 | A | 10/1998 | Davis et al. |
| 6,018,676 | A | 1/2000 | Davis et al. |
| 6,513,527 | B1 * | 2/2003 | Abdel-Aziz ............ 128/207.14 |
| 2007/0179508 | A1 * | 8/2007 | Arndt ............................ 606/116 |

FOREIGN PATENT DOCUMENTS

| WO | 2008/0148165 | 12/2008 |
| WO | 2009/0063166 | 5/2009 |

* cited by examiner

*Primary Examiner* — Jonathan Cwern
(74) *Attorney, Agent, or Firm* — Fay Kaplun & Marcin, LLP

(57) ABSTRACT

A medical device comprises a cannula for insertion to a target location in a body and at least one resonator situated on a surface of the cannula. The resonator resonates in response to an ultrasonic frequency applied to the target location to indicate the location of the cannula in the body. The ultrasonic frequency is generated by a transducer located external to the body. The medical device also comprises a device converting resonated frequencies into an image.

31 Claims, 4 Drawing Sheets

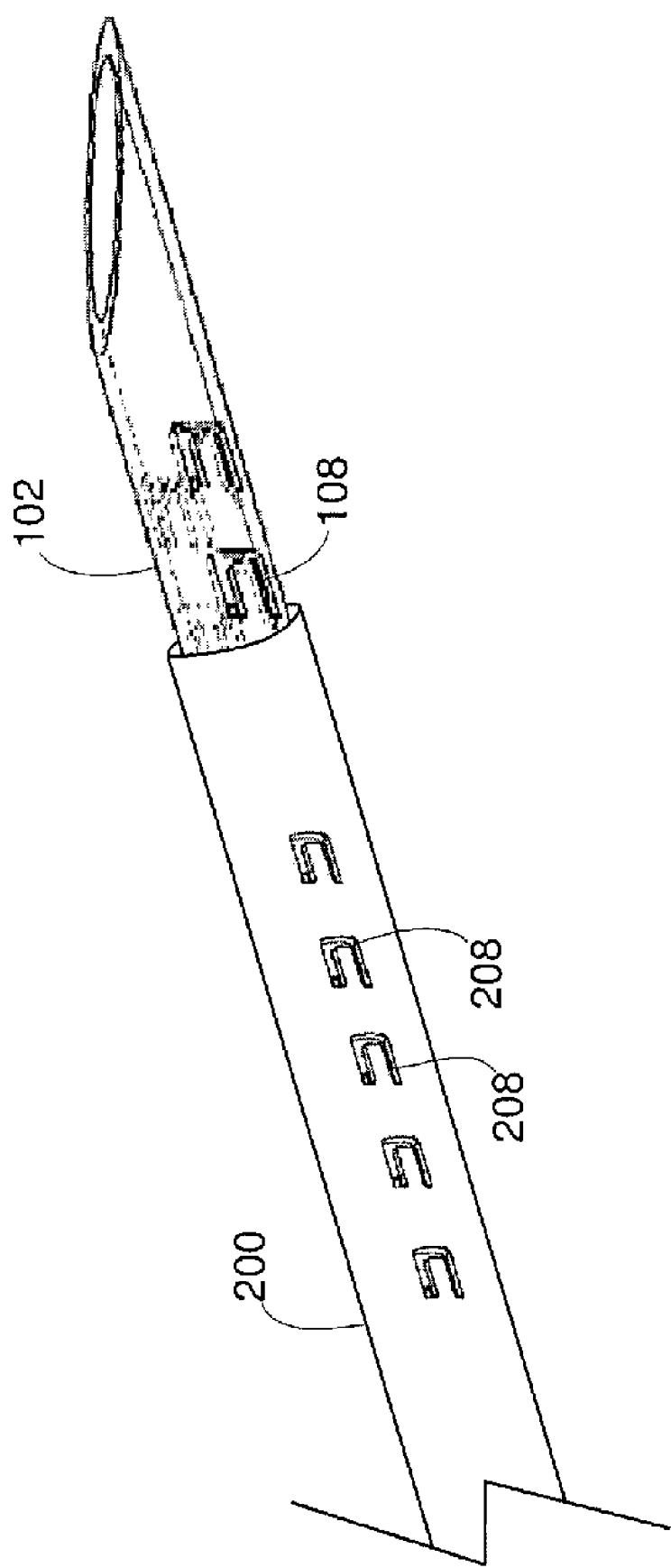

ECHOGENIC NEEDLE MECHANISM

PRIORITY CLAIM

The present application claims the priority to the U.S. Provisional Application Ser. No. 61/245,454, entitled "ECHOGENIC NEEDLE MECHANISM" filed on Sep. 24, 2009. The specification of the above-identified application is incorporated herewith by reference

BACKGROUND

Needle catheters are often employed to inject fluids and/or obtain fluid or tissue samples for diagnosis and/or treatment. In these procedures, a needle is advanced to a target tissue site within a catheter under ultrasound guidance. The needle may be advanced distally from the catheter to penetrate the target site. The ultrasound image can allow a user to visualize the position of the needle in relation to the target and surrounding structures and aids in ensuring that a correct tissue portion is treated, sampled, etc. to minimize the risk of trauma or injury to non-targeted tissue. A common challenge associated with the use of ultrasound imaging is the relatively low echogenicity of the needle and the lack of clarity in the resulting images.

As would be understood by those skilled in the art, several factors play a role in the echogenicity of the needle including needle gauge, the difference in acoustic impedance between the needle and the surrounding tissue, the angle of the needle relative to the transducer, the frequency being used and various characteristics of the processing algorithm.

SUMMARY OF THE INVENTION

A medical device according to the present invention comprises a cannula for insertion to a target location in a body and at least one resonator situated on a surface of the cannula, the resonator resonating in response to an ultrasonic frequency applied to the target location to indicate the location of the cannula in the body, wherein the ultrasonic frequency is generated by a transducer located external to the body. The medical device also comprises a device converting resonated frequencies into an image.

BRIEF DESCRIPTION OF THE DRAWINGS

FIG. 5 shows a side view of a needle according to a fourth exemplary embodiment of the present invention.

DETAILED DESCRIPTION

The present invention, which may be further understood with reference to the following description and the appended drawings, relates to a device to enhance the ultrasonic visibility of a needle when deployed within the body to perform a procedure such as, for example, a needle biopsy. It is noted, however, that although the exemplary embodiments of the present invention are described with respect to particular procedures, the description is not meant to limit the application of the invention, which may be employed in any of a number of procedures requiring the insertion of a needle to a target site within the body.

Devices and methods according to exemplary embodiments of the invention enhance the visibility of a needle when deployed, for example, from a catheter to a target site within the body. Specifically, exemplary embodiments of the present invention seek to enhance the echogenicity of a needle in situ by providing resonating features thereupon, the resonating features designed to resonate at a predetermined frequency which may be applied thereto via an ultrasound transducer or another means known in the art. Any of a variety of known mechanical arrangements may be employed to generate a mechanical force at a distal portion of the catheter for the deployment of the needle therefrom. This invention is not restricted to needles but may also be applicable to any number of cannulas or catheters to a visualized remotely by, for example, ultrasound. In one example, the present invention may be employed in an ablation device.

Figure 1:
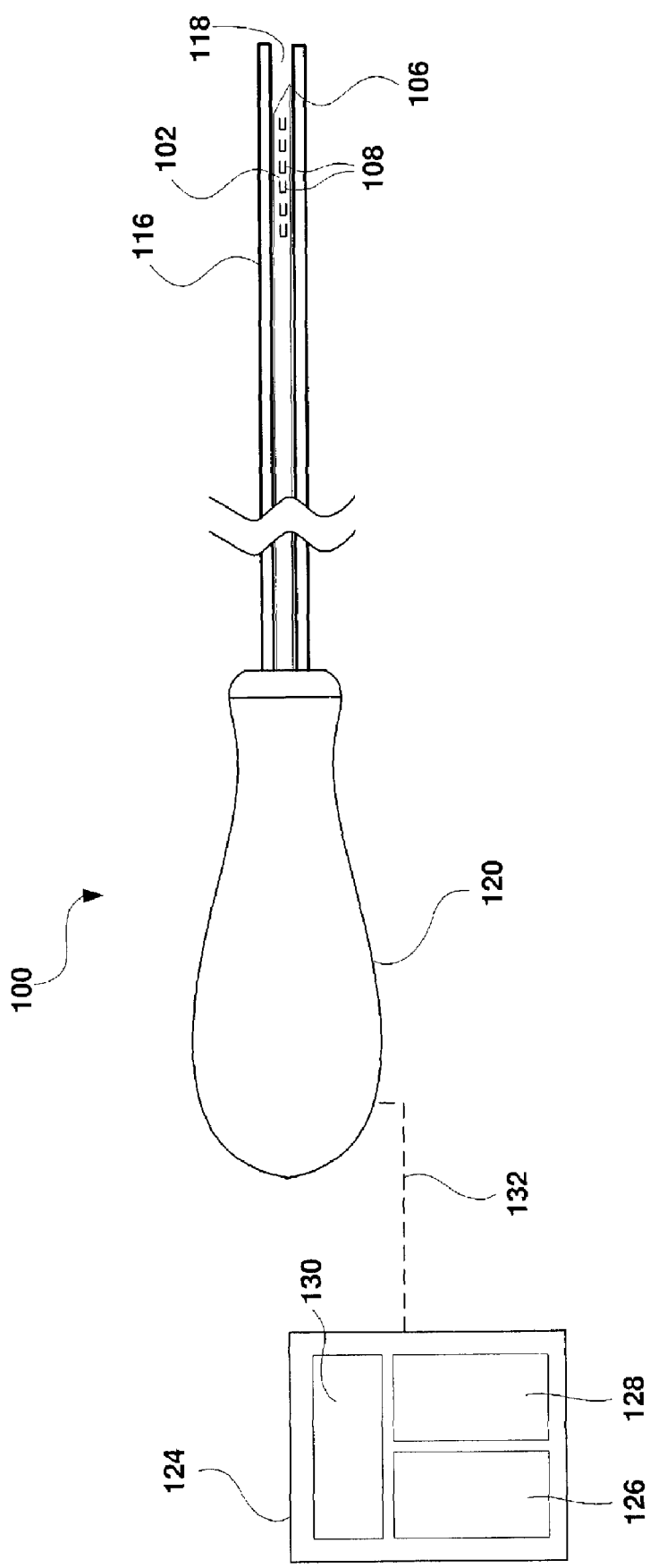
FIG. 1 shows a side view of an exemplary device according to the present invention.
Figure 2:
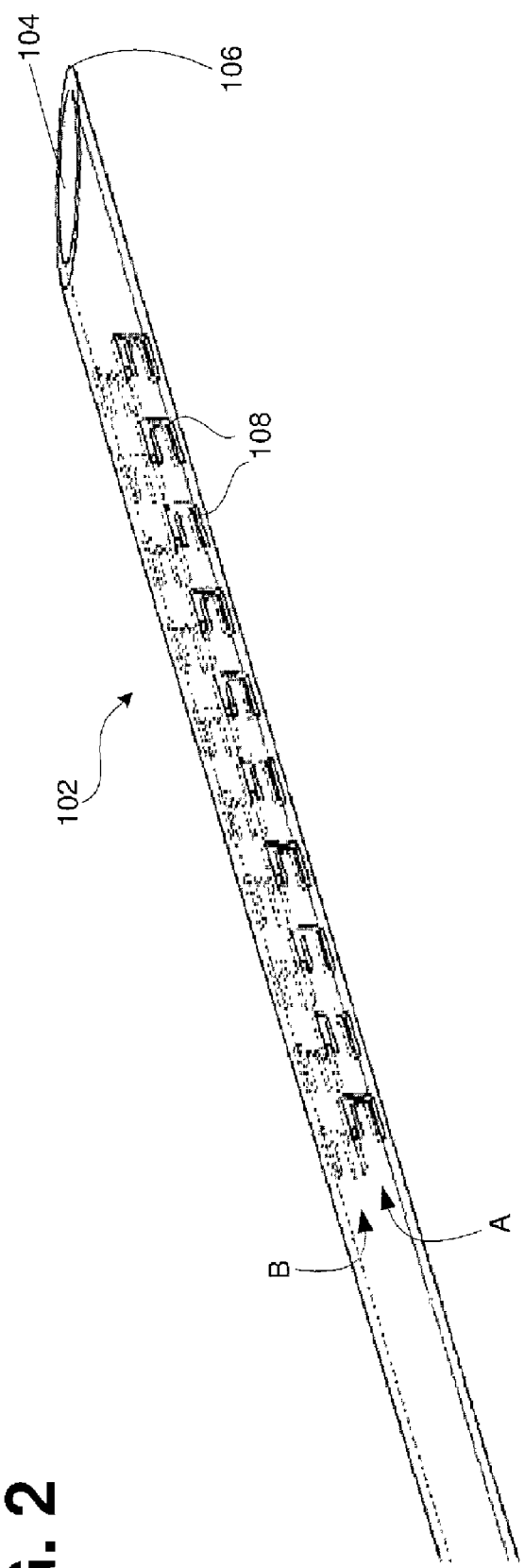
FIG. 2 shows a side view of a needle according to a first exemplary embodiment for use with the device of FIG. 1.

As shown in FIGS. 1 and 2, a device 100 according to a first exemplary embodiment of the present invention comprises a needle 102 having a tubular body with a lumen 104 extending therethrough from a proximal end extending into a handle 120 to a distal end comprising a puncturing tip 106. It is noted that the use of the term distal herein refers to a direction away from a user of the device while the term proximal refers to a direction approaching a user of the device. The proximal portion of the device 100, including the handle 120, remains external to the body and accessible to the user while the distal portion, when in an operative position, extends into the body to a target site from which tissue samples are to be obtained in accordance with the biopsy procedure. A shaft 116 of the device 100 and the needle 102 may be rigid or, alternatively, may be longitudinally flexible and axially rigid to allow for the insertion of the shaft 116 and the needle 102 along a tortuous path (e.g., through a body lumen) to a target site within the body. The needle 102 may be formed of any suitable biocompatible material known in the art depending on the desired properties of the needle (e.g., rigidity/flexibility, etc.).

A series of circumferentially aligned beams 108 are formed along at least one longitudinal length of the needle 102. In a preferred embodiment, two sets of beams 108 are formed on opposite sides A and B (shown in phantom) of the needle 102, as shown in FIG. 2. The beams 108 may be provided over any part of the needle 102 without deviating from the scope of the present invention. The beams 108 may be cantilever beams formed, for example, by laser micromachining or micro-stamping the outer surface of the needle 102. Alternatively, a surface micromachining process may be used to deposit or etch beams 108 onto the surface of the needle 102. In an alternate embodiment, the beams 108 located on opposite sides A and B may also be formed in different configurations, so as to distinguish an orientation of the needle 102 in situ, as those skilled in the art will understand. Specifically, shapes and sizes of the beams 108 on opposite sides A and B may be distinguishably varied from one another so that an orientation of the needle 102 can be determined based on the location of sides A and B in situ. It is preferred, however, to maintain similar resonance requirements on each side A and B so that both sides are locatable at least one predetermined frequency.

The dimensions of each of the beams 108 may also be varied depending on the type of procedure being performed so that the natural frequency of the beams 108 coincides with the ultrasonic frequency of interest, as those skilled in the art will understand. If a particular procedure requires the targeting of more than one ultrasound frequency (i.e., to overcome excessive noise encountered at a first frequency, etc.), the beams 108 may be formed with different dimensions to accommodate the plurality of frequencies. Such an embodiment will aid in the location of the needle 102 in the body when any of the plurality of target frequencies are employed. Furthermore, in a preferred embodiment, beams 108 of different natural frequencies are evenly distributed along the needle 102, such as, for example, in an alternating pattern. In one embodiment, the frequencies may include 5 MHz and 7.5 MHz, although any other frequencies may be employed without deviating from the scope of the present invention. Furthermore, the beams 108 may have varying geometries including, but not limited to rectangular, square and triangular and may also have varying thickness, widths and heights. The beams 108 may also comprise any combination and plurality of holes, cutouts, slots, slits, bends and other surface features (e.g., peaks, valleys, etc.) without deviating from the scope of the present invention.

The beams 108 function as resonators in the needle, as those skilled in the art will understand. When used under ultrasound guidance, the acoustic energy from an ultrasound transducer located external to the body when in an operative configuration causes the beams 108 to resonate, thus providing an ultrasonic image of the needle 102.

Figure 3:
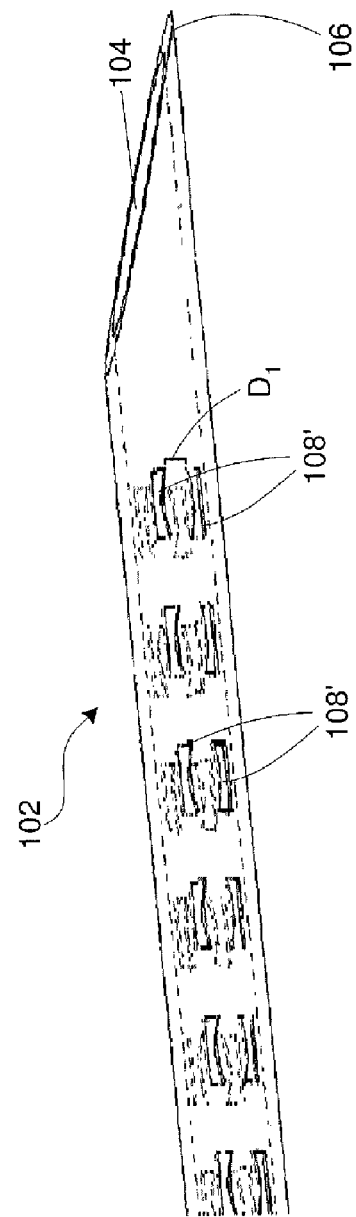
FIG. 3 shows a side view of a needle according to a second exemplary embodiment for use with the device of FIG. 1.

Those skilled in the art will understand that cantilever beams can resonate to any multiple of their fundamental frequency. Altering the geometry of the beams 108 can increase the fundamental frequency. For example, as shown with respect to FIG. 3, beams 108' can be formed to resemble two adjacent arced pieces lying along a longitudinal length of the needle 102, wherein the adjacent pieces are separated from one another by a distance $D_1$. The distance $D_1$, along with other dimensional values of the beams 108' is indicative of the resonating frequency thereof. Since the two arced pieces are not joined together at a proximal end, resonance can be increased, as those skilled in the art will understand. It is noted that any configuration of the beams 108 may be employed without deviating from the spirit and scope of the present invention.

Figure 4:
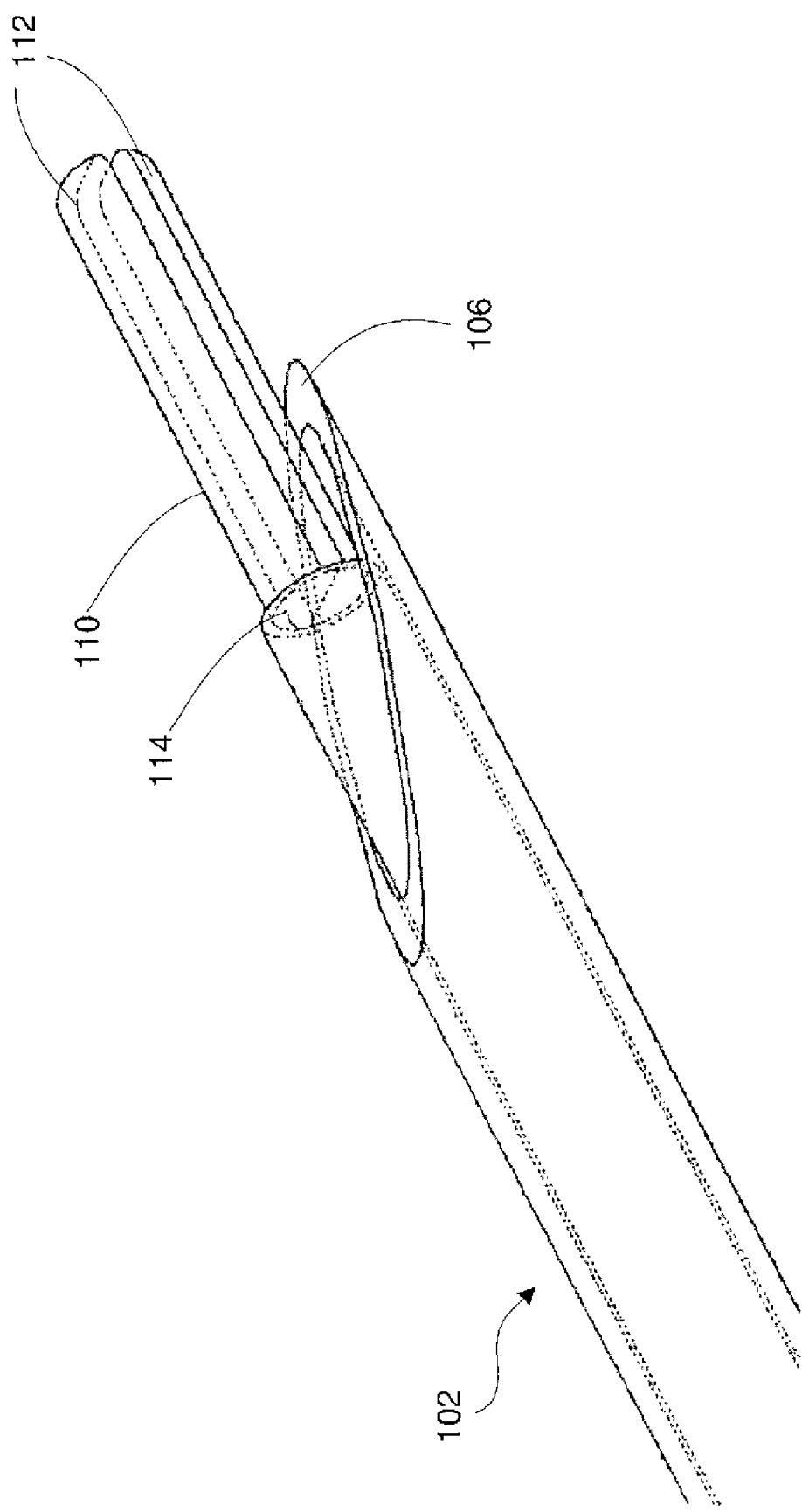
FIG. 4 shows a side view of a needle according to a third exemplary embodiment for use with the device of FIG. 1.

Resonance in the device of the present invention may also be improved by providing a resonating stylet 110 to be used with the needle 102. The resonating stylet 110 would not have to be employed in conjunction with the needle 102 comprising the beams 108. Rather, the resonating stylet 110 may function with any medical device within which the stylet 110 may be received. Specifically, as shown in FIG. 4, the stylet 110 may be formed in a cantilever shape, wherein a distal portion of the stylet 110 is formed with two legs 112 spaced from one another and joined to a proximal portion of the stylet at a juncture 114. The legs 112 may be formed as a unitary element with the stylet 110 or, alternatively, may be formed separately and attached thereto via a means known in the art such as bonding, welding, etc. A distal portion of the stylet 110 serves as a resonator, wherein the dimensions of the legs 112 may dictate the appropriate resonance frequency for the ultrasound. In one embodiment, the resonance frequency of the cantilever may be approximately 5 MHz to conform to available ultrasound systems, although any other frequency may also be employed without deviating from the scope of the present invention. In a further embodiment of the present invention, the stylet 110 may also be provided with beams 108 or 108' to further improve imaging or to enable visualization of the stylet 110 under a plurality of frequencies, as explained earlier. Specifically, the beams 108 or 108' may be formed as cut-outs formed in the stylet or may be abutments bonded or otherwise attached to the outer surface of the stylet 110. It is noted that the device of the present invention is not limited to the stylet 110 as depicted but may employ any stylet known in the art. Similarly, the stylet of the present invention may be employed with any device comprising ultrasonic resonators.

In an alternate embodiment of the present invention, fabrication of the beams 108 of the present invention may be done using the same manufacturing technology used for electrical circuit or micro-electrical mechanical systems ("MEMS"). In this manner, a resonant mechanical system may be produced for one or more frequencies of interest. In yet another alternate embodiment, a micro-miniature ultrasonic transducer may be mounted on one or both of the needle 102 or the stylet 110 of the present invention. The micro-miniature ultrasonic transducer may function as a transmitter insertable into the body, with the external ultrasound device functioning as a receiver, as those skilled in the art will understand.

In use, the needle 102 is received within a lumen 118 extending through a catheter shaft 116, the lumen 118 is sized to slidably receive the needle 102 with a clearance between the needle 102 and an inner wall of the lumen 118.

Those skilled in the art will understand that cantilever beams can resonate to any multiple of their fundamental frequency. Altering the geometry of the beams 108 can increase the fundamental frequency. For example, as shown with respect to FIG. 3, beams 108' can be formed to resemble two adjacent arced pieces lying along a longitudinal length of the needle 102, wherein the adjacent pieces are separated from one another by a distance $D_1$. The distance $D_1$, along with other dimensional values of the beams 108' is indicative of the resonating frequency thereof. Since the two arced pieces are not joined together at a proximal end, resonance can be increased, as those skilled in the art will understand. It is noted that any configuration of the beams 108 may be employed without deviating from the spirit and scope of the present invention.

Resonance in the device of the present invention may also be improved by providing a resonating stylet 110 to be used with the needle 102. The resonating stylet 110 would not have to be employed in conjunction with the needle 102 comprising the beams 108. Rather, the resonating stylet 110 may function with any medical device within which the stylet 110 may be received. Specifically, as shown in FIG. 4, the stylet 110 may be formed in a cantilever shape, wherein a distal portion of the stylet 110 is formed with two legs 112 spaced from one another and joined to a proximal portion of the stylet at a juncture 114. The legs 112 may be formed as a unitary element with the stylet 110 or, alternatively, may be formed separately and attached thereto via a means known in the art such as bonding, welding, etc. A distal portion of the stylet 110 serves as a resonator, wherein the dimensions of the legs 112 may dictate the appropriate resonance frequency for the ultrasound. In one embodiment, the resonance frequency of the cantilever may be approximately 5 MHz to conform to available ultrasound systems, although any other frequency may also be employed without deviating from the scope of the present invention. In a further embodiment of the present invention, the stylet 110 may also be provided with beams 108 or 108' to further improve imaging or to enable visualization of the stylet 110 under a plurality of frequencies, as explained earlier. Specifically, the beams 108 or 108' may be formed as cut-outs formed in the stylet or may be abutments bonded or otherwise attached to the outer surface of the stylet 110. It is noted that the device of the present invention is not limited to the stylet 110 as depicted but may employ any stylet known in the art. Similarly, the stylet of the present invention may be employed with any device comprising ultrasonic resonators.

FIG. 5 depicts a system according to an alternate embodiment of the present invention, wherein the device is formed substantially similarly to the device 100 of FIG. 1 with the exception of a sheath 200 provided over an outer surface of the needle 102. The sheath 200 may be provided with resonators 208 distributed thereover in any configuration. The resonators 208 may be formed as cutouts on the sheath 200 or abutments bonded or otherwise attached to the sheath 200 and may be configured to enhance the resonance of the beams 108 of the needle 102, as those skilled in the art will understand. In use, the sheath (not shown) may be provided over the needle 102 and, once the catheter shaft 116 is positioned in a desired location relative to a target site in the body, the ultrasonic scanner 124 and transducer 128 may be operated as described above to aid in visualization of the needle 102.

The present invention may be applied to any procedure requiring the insertion of a needle into tissue via a device traversing a tortuous path. Though the present invention has been described with respect to the retrieval of tissue samples, it is submitted that devices for alternate uses such as, for example, needles for injection of fluids to or the withdrawal of fluids from the body may employ to invention without deviating from the spirit and scope of the present invention. Thus, these embodiments have been described in an exemplary manner and are not intended to limit the invention which is intended to cover all modifications and variations of this invention that come within the scope of the appended claims and their equivalents. For example, the beams of the present invention may be formed separately from the needle and can be subsequently bonded to the needle via a means known in the art. Furthermore, it is noted that the ultrasonic resonators of the present invention are not restricted for use with needles and rather, may be employed in any medical device visualized by the use of ultrasound. It is therefore submitted that the embodiments disclosed herein are not limited to limit the scope of the present invention.

What is claimed is:

1. A medical device, comprising:
    a cannula configured to be inserted into a target location in a body;
    at least one resonator situated on a surface of the cannula, the at least one resonator resonating in response to an ultrasonic frequency applied to the target location to produce resonated frequencies indicative of the location of the cannula in the body, wherein the ultrasonic frequency is generated by a transducer located external to the body, wherein the at least one resonator includes a cantilever beam oriented along a longitudinal axis of the cannula; and
    a processor converting the resonated frequencies produced by the at least one resonator into an image.

2. The medical device according to claim 1, further comprising: a handle located at a proximal end of the cannula.

3. The medical device according to claim 1, wherein the at least one resonator corresponds to one of a cut-out and an abutment on an outer surface of the cannula.

4. The medical device according to claim 1, wherein the at least one resonator is etched into an outer surface of the cannula.

5. The medical device according to claim 1, wherein the at least one resonator is formed via one of laser micromachining, microstamping, MEMS and surface machining.

6. The medical device according to claim 5, wherein the at least one resonator is bonded to the cannula.

7. The medical device according to claim 1, wherein the at least one resonator is dimensioned to resonate at least one predetermined frequency.

8. The medical device according to claim 1, further comprising: a stylet including at least one resonating feature for resonating when actuated by sound waves.

9. The medical device according to claim 8, wherein stylet includes a cantilever.

10. The medical device according to claim 9, wherein a distal portion of the stylet includes two legs spaced from one another and joined to a proximal portion of the stylet at a juncture.

11. The medical device according to claim 8, wherein a resonator is bonded to an outer wall of the stylet.

12. The medical device according to claim 1, wherein a plurality of resonators are formed on the cannula.

13. The medical device according to claim 12, wherein the resonators are aligned along a longitudinal axis of the cannula.

14. The medical device according to claim 1, wherein the cantilever is anchored in a material of the cannula.

15. The medical device according to claim 1, wherein the cantilever is a cutout in the cannula.

16. The medical device according to claim 1, wherein only a first end of the cantilever is anchored in a material of the cannula.

17. The medical device according to claim 1, wherein the cantilever is a rectangular beam.

18. A medical device, comprising:
    a cannula configured to be inserted into a target location in a body;
    a sheath configured to be received over the cannula in an insertion configuration;
    at least one first resonator situated on a surface of the sheath, the at least one first resonator resonating in response to an ultrasonic frequency applied to the target location to produce resonated frequencies indicative of the location of the sheath and cannula in the body, wherein the ultrasonic frequency is generated by a transducer located external to the body, wherein the at least one first resonator includes a cantilever beam oriented along a longitudinal axis of the sheath; and
    a processor converting the resonated frequencies produced by the at least one first resonator into an image.

19. The medical device according to claim 18, wherein the at least one first resonator includes one of a cut-out and an abutment on an outer surface of the sheath.

20. The medical device according to claim 18, wherein the at least one first resonator is dimensioned to resonate at at least one predetermined frequency.

21. The medical device according to claim 18, further comprising: at least one second resonator provided on the cannula, the at least one second resonator resonating in response to an ultrasonic frequency applied to the target location.

22. The medical device according to claim 18, wherein the cantilever is anchored in a material of the sheath.

23. The medical device according to claim 18, wherein the cantilever is a cutout in the sheath.

24. The medical device according to claim 18, wherein only a first end of the cantilever is anchored in a material of the sheath.

25. The medical device according to claim 18, wherein the cantilever is a rectangular beam.

26. A medical device, comprising:
    a cannula configured to be inserted into a target location in a body;

a stylet configured to be inserted through the cannula;

at least one first resonator provided on the stylet, the at least one first resonator resonating in response to an ultrasonic frequency applied to the target location to produce resonated frequencies indicative of the location of the cannula in the body, wherein the ultrasonic frequency is generated by a transducer located external to the body wherein the at least one first resonator includes a cantilever including a plurality of legs spaced from one another and extending from a proximal portion of the stylet oriented along a longitudinal axis of the style; and a processor converting the resonated frequencies produced by the at least one first resonator into an image.

27. The medical device according to claim 26, further comprising: at least one second resonator provided on the cannula, the at least one second resonator resonating in response to an ultrasonic frequency applied to the target location.

28. A method for accessing tissues within a body, comprising:

inserting into a body a distal end of a cannula including at least one resonator on a surface portion, the resonator adapted to resonate when subjected to a predetermined sound frequency, wherein the resonator includes a cantilever beam oriented along a longitudinal axis of the cannula; and generating a predetermined sound frequency and directing the sound frequency to the cannula, wherein the resonator creates a responsive resonating frequency, the resonated frequency being detected by a sensor and converted into an image.

29. The method according to claim 28, further comprising: deploying the cannula into the body when properly positioned at a target site in the body.

30. The method according to claim 28, further comprising: generating a second predetermined sound frequency and directing the second predetermined sound frequency to the cannula, wherein the resonator creates a responsive resonating frequency.

31. The method according to claim 28, wherein the image is displayed in real time.

\* \* \* \* \*